United States Patent [19]

Pilgram et al.

[11] 4,308,389
[45] Dec. 29, 1981

[54] SPIRO-$\Delta^3$-1,2,3-THIADIAZOLINES AND A METHOD FOR THE PREPARATION THEREOF

[75] Inventors: Kurt H. Pilgram; Richard D. Skiles, both of Modesto, Calif.

[73] Assignee: Shell Oil Company, Houston, Tex.

[21] Appl. No.: 221,954

[22] Filed: Dec. 31, 1980

[51] Int. Cl.$^3$ .................... A01N 43/82; C07D 285/14
[52] U.S. Cl. ........................................ 548/127; 71/90; 564/147; 564/148
[58] Field of Search ........................................ 548/127

[56] References Cited
U.S. PATENT DOCUMENTS 2,895,958  7/1959  Friedlander ........................ 548/127
3,037,027  5/1962  Dodson et al. ...................... 548/127

*Primary Examiner*—Alton D. Rollins

[57] ABSTRACT

Spiro-$\Delta^3$-1,2,3-thiadiazolines of the formula:

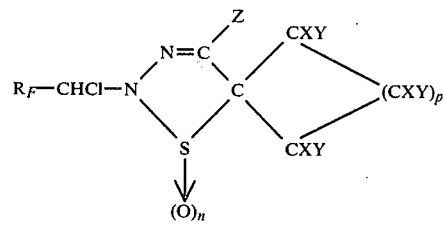

wherein $R_F$ represents a perfluoroalkyl group having from 1 to 6 carbon atoms, each X and each Y is independently selected from the class consisting of hydrogen, halogens, lower alkyl, and halogen-substituted lower alkyl, Z is fluorine, chlorine, or bromine, p is an integer from 2 to 6, and n is either 1 or 2; and a method for the preparation of such compounds comprising the reaction of certain acylated perfluorinated aliphatic aldehyde hydrazones with a thionyl halide.

6 Claims, No Drawings

SPIRO-Δ³-1,2,3-THIADIAZOLINES AND A METHOD FOR THE PREPARATION THEREOF

This invention relates to certain spiro-Δ³-1,2,3-thiadiazoline derivatives and to a method for their preparation.

A limited number of representatives of the Δ³-1,2,3-thiadiazoline ring system are known. Compounds of the formula

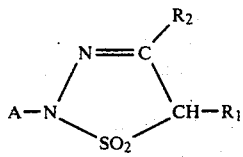

wherein A is phenyl, $R_1$ is hydrogen, methyl, or isopropyl, and $R_2$ is methyl or p-tolyl, have been prepared by the action of phosphorous trichloride on the corresponding phenylhydrazones of salts of beta-ketosulfonic acids (A. P. Terentyev et al, *J. Gen. Chem. USSR* (English translation), 26, 3859 (1956)). One of such compounds has been shown to exhibit antimicrobial activity.

The compound of the formula

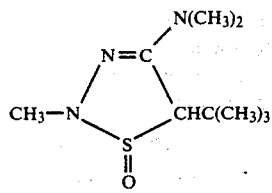

has been reported by R. Buyle and H. G. Viehe (*Tetrahedron*, 24, 3987 (1968)). This compound was prepared by reaction of methyl hydrazine with the product of the addition of thionyl chloride to 3,3,N,N-tetramethyl-1-butyn-1-amine.

SUMMARY OF THE INVENTION

There have now been discovered novel spiro-Δ³-1,2,3-thiadiazoline derivatives of formula I,

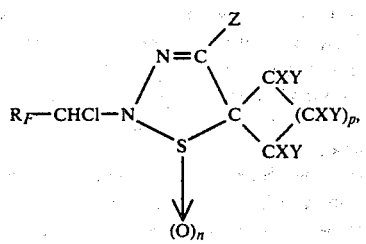

wherein $R_F$ is perfluoroalkyl, each X and each Y is independently selected from the group consisting of hydrogen, halogens, lower alkyl, and halogen-substituted lower alkyl, Z is selected from the class consisting of fluorine, chlorine, and bromine, p is an integer greater than 1, and n is the integer 1 or the integer 2. It has also been found that compounds of formula I are prepared by means of a process comprising the reaction of thionyl chloride (to yield a compound of formula I in which Z is chlorine), thionyl bromide (for a compound in which Z is bromine), or thionyl fluoride (for a compound in which Z is fluorine) with acylated perfluorinated aliphatic aldehyde hydrazones of formula II,

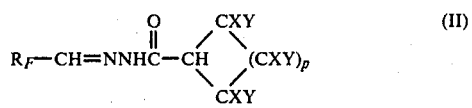

wherein $R_F$ and p are as defined for formula I. Still further, it has been found that the novel compounds of formula I have useful biological properties.

It is considered most unexpected that the compounds of formula I are prepared in the above described manner. In earlier investigations of the reactions of perfluorinated aliphatic aldehyde aroylhydrazones, it was found that reaction with thionyl chloride under conditions similar to those suitable for the process of the invention yielded 1-aryl-1-chloro-4-(perfluoroalkyl)azines. For instance, there has been disclosed (*J. Org. Chem.*, 41, 3392 (1976), and *J. Agric. Food Chem.*, 25, 888 (1977)) the reaction

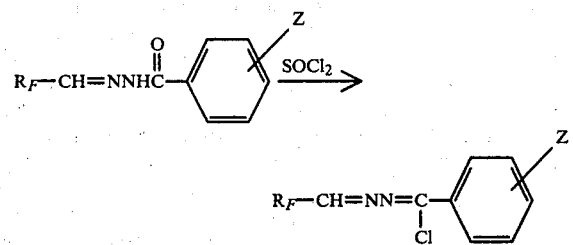

which was not accompanied by formation of spiro thiadiazoline derivatives.

Novel compounds of formula I, wherein $R_F$ represents a perfluoroalkyl group having one to four carbon atoms, p is an integer from two to four, inclusive, each X and each Y represents hydrogen, Z is fluorine, chlorine, or bromine, and n is the integer one or the integer two, are particularly preferred. More preferred are the compounds wherein $R_F$ represents a perfluoroalkyl group having one, two or three carbon atoms and p is the integer two or the integer three.

DESCRIPTION OF THE PREFERRED EMBODIMENTS

The cyclization reaction of the thionyl halide, i.e., fluoride, chloride, or bromide, with the acylated perfluorinated aliphatic aldehyde hydrazones of formula II, said hydrazones consisting of a mixture of geometric (syn and anti) isomers, produces two pairs of diastereoisomeric spiro-heterocyclic compounds according to formula I where n is the integer one. It is to be understood that each of the isomer configurations, as well as mixtures of isomers are included in the present invention. The nature of the particular isomer configuration has not been found to have a great effect upon the herbicidal activity of the compounds of the invention.

Preparation of thiadiazoline derivatives according to the reaction process of the invention is carried out in liquid solution. Advantageously, the reaction can be accomplished simply by dissolving the hydrazone starting material in an excess of the thionyl halide reactant, in which case the reaction solution preferably comprises between about 1 and 12, most preferably between about 1.5 and 8, mols of the thionyl halide per mol of the hydrazone. There is, as a general rule, no need for the use of an additional solvent in the liquid reaction solution of the process, although an inert solvent, e.g., benzene, can be employed if desired.

The condensation reaction of the hydrazone with the thionyl halide for purposes of the invention is suitably carried out at a temperature in the range of 20° to 140° C., preferably at a temperature in the range of about 40° to 120° C., more preferably in the range of about 70° to 95° C. Temperatures above approximately 140° C., known to result in decomposition of the suitable thionyl halides, are to be avoided. Reaction pressure must be such that the reactants will remain in liquid solution. A pressure of one atmosphere is most preferred.

The reaction for preparation of thiadiazoline derivatives in accordance with the invention is carried out in the presence of a catalyst, which is preferably an amide or an organic nitrogen-containing base soluble in the reaction mixture. Dimethylformamide and tertiary aromatic or highly alkylated amines, particularly pyridine and pyridine derivatives, are a most preferred group of catalysts for the desired reaction. The quantity of catalyst present has not been found to have a critical influence upon the success of the process. To obtain good conversion to the desired thiadiazoline compounds at a rapid rate, it is preferred that the hydrazone, thionyl halide liquid reaction mixture contain at least about 0.01 percent by weight of the catalyst. More preferably, the mixture contains catalyst in an amount between about 0.1 and 10 percent by weight. The catalyst can suitably be employed in quantities substantially greater than 10 percent by weight, although such greater quantities do not further benefit the process. Most preferably, the reaction mixture contains between about 0.2 and 5 percent by weight of the catalyst.

The acylated perfluorinated aliphatic aldehyde hydrazone starting materials (formula II), used in preparation of the desired thiadiazoline derivatives, are themselves suitably prepared by the reaction of a perfluorinated aliphatic aldehyde III (or the corresponding aldehyde hydrate or hemi-acetal) and a $C_5$–$C_9$-cycloalkanecarboxylic acid hydrazide (IV), i.e.,

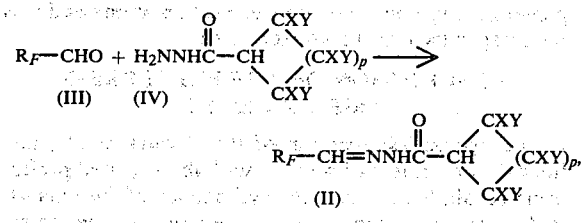

according to methods known in the art and exemplified herein.

For purposes of preparing the desired thiadiazoline derivatives, according to the invention, it is critical that p represent, in the illustration of the hydrazone starting materials in formula II, an integer greater than one. Reaction of a hydrazone having a four-membered aliphatic ring, i.e., formula II wherein p is one, did not yield a spiro-$\Delta^3$-1,2,3-thiadiazoline. Preferably, p is an integer from 2 to 6, more preferably an integer from 2 to 4, most preferably either 2 or 3.

Suitable X and Y substituents of the alkane ring structure of the hydrazone starting materials are each individually selected from the group consisting of hydrogen, halogens, lower alkyl having 1 to 4 carbon atoms, and halogen-substituted lower alkyl having one to 4 carbon atoms. Preferably each X and each Y is either hydrogen, halogen or methyl; most preferably each X and each Y is hydrogen.

No criticality has been observed with regard to carbon number of the $R_F$ perfluoroalkyl moiety for purposes of preparing the thiadiazolines from the hydrazones. Preferably the $R_F$ substituent of the hydrazone starting material comprises between about 1 and 6 carbon atoms inclusive, more preferably between about 1 and 4 carbon atoms inclusive, most preferably either 1, 2, or 3 carbon atoms. The perfluoro character of the $R_F$ substituent is, however, critical to the desired preparation according to the process of the invention. Attempts to prepare spiro-$\Delta^3$-1,2,3-thiadiazolines by the reaction of hydrazones having perchloro substituents have failed.

The reaction of hydrazones of formula II with thionyl fluoride thionyl chloride, or thionyl bromide yields novel thiadiazoline S-oxide derivatives of formula I, i.e., wherein n=1. The S-oxide is, however, readily converted into the S,S-dioxide by reaction with an oxidizing agent, preferably a peracid such as meta-chloroperbenzoic or peracetic acid. It is considered that the invention, insofar as it relates to novel thiadiazoline compounds, includes both the S-oxide (n=1) and the S,S-dioxide (n=2) derivatives of formula I.

The following examples, comparative examples and illustrative embodiments illustrate the thiadiazoline derivatives of the invention, the process for their preparation, and their herbicidal activity. Preparations of the acylated perfluorinated aliphatic aldehyde hydrazones, which are employed in the synthesis of the subject thiadiazoline compounds, are also described.

EXAMPLE 1

Preparation of 1-thia-2,3-diazaspiro(4.4)non-3-ene, 4-chloro-2-(1-chloro-2,2,2-trifluoroethyl)-, 1-oxide, of formula I, wherein $R_F$ is $CF_3$, each X and each Y is hydrogen, Z is chlorine, p is 2, and n is 1.

A solution of 59.0 grams (0.284 mol) of cyclopentanecarboxylic acid (2,2,2-trifluoroethylidene)hydrazide and 5 milliliters of dimethylformamide in 150 milliliters of thionyl chloride was refluxed with stirring for 2.5 hours. Excess thionyl chloride was then removed by rotary evaporation. The evaporation residue was extracted with boiling hexane, and the extract was decolorized with charcoal, cooled, and filtered to yield 6.0 grams of a colorless solid. Adsorption of the solid on silica gel, followed by chromatographic separation over silica, using an eluent containing 80% by volume (%v) hexane, 16%v ethyl acetate, and 4%v tetrahydrofuran, yielded about 0.7 gram of the title compound with a melting point of 114°–117° C.

Analysis (percent by weight). Found: C, 31.5, H, 3.0; N, 9.2. Calculated: C, 31.1; H, 2.9; N, 9.1.

No attempt was made to separate product isomers.

The cyclopentanecarboxylic acid (2,2,2-trifluoroethylidene)hydrazide (formula II wherein $R_F$ is $CF_3$, each X and each Y is hydrogen, and p is 2) utilized in the preparation according to this example was obtained by the following procedure. A solution of 48.6 grams (0.38 mol) of cyclopentanecarboxylic acid hydrazide and 80.0 grams (0.69 mol) of trifluoroacetaldehyde hydrate in 500 milliliters of benzene was heated to reflux for 18 hours. Water was removed azeotropically as formed. The resulting reaction mixture was concentrated to a volume of 200 milliliters by rotary evaporation, then diluted with 600 milliliters of hexane, cooled to 5° C. and filtered to recover 60 grams of the desired compound as a colorless solid, melting point 147°–150° C.

Analysis (percent by weight), Found: C, 46.1; H, 5.4; N, 13.8. Calculated: C, 46.2; H, 5.3; N, 13.5.

EXAMPLE 2

Preparation of 1-thia-2,3-diazaspiro(4.5)dec-3-ene, 4-chloro-2-(1-chloro-2,2,2-trifluoroethyl)-, 1-oxide, of formula I, wherein $R_F$ is $CF_3$, each X and each Y is hydrogen, Z is chlorine, p is 3, and n is 1.

A solution containing 51.9 grams (0.234 mol) of cyclohexanecarboxylic acid (2,2,2-trifluoroethylidene)hydrazide in 110 millileters of thionyl chloride was stirred and refluxed at 82° C. for 2.5 hours without change detectable by thin layer chromatography. Ten drops of dimethylformamide were added and heating was then continued for an additional 2.5 hours. Thin layer chromatography disclosed that all of the starting material had reacted; two product compounds were detected. Excess thionyl chloride was removed from the reaction mixture by rotary evaporation leaving 71 grams of residual solid. Recrystallization from hexane with decolorization over charcoal yielded 48 grams of a colorless solid mixture of isomers of the title compound with a melting point of 96°–101° C. Ten grams of this mixture was chromatographed over silica gel with an 80%v hexane, 15%v ethyl acetate, 4%v tetrahydrofuran eluent to give 2.75 grams of a first isomer fraction, melting point 100° C.–102° C., and 5.5 grams of a second fraction, melting point 119°–121° C.

Analysis of the first fraction (percent by weight). Found: C, 33.7; H, 3.4; Cl, 21.9; N, 8.5; S, 10.1 Calculated: C, 33.4; H, 3.4; Cl, 22.0; N, 8.7; S, 9.9.

Analysis of the second fraction (percent by weight). Found: C, 33.5; H, 3.3; Cl, 21.9; N, 8.6; S, 10.2.

Identity of the product was confirmed by infrared spectral analysis and by nuclear magnetic resonance spectral analysis of each isomer fraction.

The cyclohexanecarboxylic acid 2,2,2-trifluoroethylidene)hydrazide (formula II wherein $R_F$ is $CF_3$, each X and each Y is hydrogen, and p is 3) used in preparation of the title compound was obtained by the following procedure. To a solution of 71.0 grams (0.5 mol) of cyclohexanecarboxylic acid hydrazide in 500 milliliters of benzene was added 106.0 grams (0.91 mol) of trifluoroacetaldehyde hydrate. The resulting mixture was stirred and gradually heated to reflux; water was removed as formed. After 18 hours, the reaction mixture was cooled, diluted with 300 milliliters of hexane, chilled to 5° C. and filtered to give 91.4 grams of the title compound as a white solid, melting point 154°–156° C.

Analysis (percent by weight). Found: C, 48.6; H, 5.9; N, 12.7. Calculated: C, 48.6; H, 5.9; N, 12.6.

EXAMPLE 3

Preparation of the 1-thia-2,3-diazaspiro(4.5)dec-3-ene, 4-chloro-2-(1-chloro-2,2,3,3,3-pentafluoropropyl)-, 1-oxide, of formula I, wherein $R_F$ is $C_2F_5$, each X and each Y is hydrogen, Z is chlorine, p is 3, and n is 1.

A solution of 74.0 grams (0.272 mol) of cyclohexanecarboxylic acid (2,2,3,3,3-pentafluoropropylidene)hydrazide and 5.0 milliliters of dimethylformamide in 150 milliliters of thionyl chloride was refluxed for 3 hours. Excess thionyl chloride was removed from the reaction mixture by rotary evaporation under vacuum, leaving 106 grams of a syrup residue containing two isomers of the title compound. A 10 gram portion of the residue was chromatographed over silica gel with an eluent containing 90%v hexane and 10%v ether to yield as a first fraction 0.5 gram of a white solid, melting point 92°–94° C., and as a second fraction 3.2 grams of a white solid melting point 92°–95° C.

Analysis of the first fraction (percent by weight). Found: C, 32.1; H, 2.9; N, 7.3. Calculated: C, 32.2; H, 2.9; N, 7.5.

Analysis of the second fraction (percent by weight). Found: C, 31.5; H, 2.8; N, 7.1. Calculated: C, 32.2; H, 2.9; N, 7.5.

The cyclohexanecarboxylic acid (2,2,3,3,3-pentafluoropropylidene)hydrazide utilized in the preparation described above is itself prepared according to the following procedure. To a stirred solution of 47.3 grams (0.333 mol) of cyclohexanecarboxylic acid hydrazide in 250 milliliters of benzene was added 80.0 grams (0.444 mol) of pentafluoropropionaldehyde methyl hemiacetal followed by 20 milliliters of 14% hydrochloric acid. The mixture was stirred at 50° C. for one hour, then heated to reflux for 18 hours, while water was removed as formed. The resulting reaction mixture was concentrated by rotary evaporation to a volume of 100 milliliters, then diluted with 300 milliliters of hexane, cooled, and filtered to yield 74.0 grams of the title compound as a colorless solid, melting point 134°–137° C.

Analysis (percent by weight). Found: C, 44.1; H, 4.8; N, 10.1. Calculated: C, 44.1; H, 4.8; N, 10.3.

EXAMPLE 4

Preparation of the 1-thia-2,3-diazaspiro(4.5)dec-3-ene, 4-chloro-2-(1-chloro-2,2,2-trifluoroethyl)-, 1,1-dioxide, of formula I, wherein $R_F$ is $CF_3$, each X and each Y is hydrogen, Z is chlorine, p is 3, and n is 2.

The title dioxide compound is prepared from the corresponding monoxide product of Example 2. To a stirred solution containing 14.0 grams (0.0435 mol) of the stereoisomeric mixture 1-thia-2,3-diazospiro(4.5)-dec-3-ene, 4-chloro-2-(1-chloro-2,2,2-trifluoroethyl)-, 1-oxide, as obtained in Example 2 before isomer separation by silica chromatography, in 100 milliliters of chloroform was added dropwise over ten minutes a solution of 8.8 grams (0.0435 mol) of 85% meta-chloroperbenzoic acid in 100 milliliters of chloroform. No change was detectable by thin layer chromatography in the resulting mixture after one hour at room temperature and one hour at 40° C. The mixture was then heated at 65°–70° C. for one hour and extracted with 5% aqueous sodium carbonate. The extract was washed with water, dried over magnesium sulfate, and concentrated to yield 14 grams of a viscous residue. Purification of the residue by silica gel chromatography resulted in 9.5 grams of an oil that crystallized from hexane to give colorless crystals of the title compound, melting point 83°–85° C.

Analysis (percent by weight). Found: C, 31.8; H, 3.3; N, 8.3. Calculated: C, 31.9; H, 3.2; N, 8.3.

COMPARATIVE EXAMPLE A

An attempt to prepare 1-thia-2,3-diazaspiro(4.5)dec-3-ene, 4-chloro-2-(1-chloro-2,2,2-trichloroethyl)-, 1-oxide according to the general procedures of the process of the invention was unsuccessful, illustrating the criticality associated with the perfluoro character of the $R_F$ substituent of the hydrazone starting material of formula II.

Cyclohexanecarboxylic acid (2,2,2-trichloroethylidene)hydrazide was prepared by refluxing a solution containing 23.0 grams (0.162 mol) of cyclohexanecarboxylic acid hydrazide and 44.2 grams (0.3 mol) of trichloroacetaldehyde in 300 ml milliliters of benzene. Water was removed as formed. After 3 hours, the reaction mixture was concentrated to a volume of 100 milliliters, diluted with 500 milliliters of hexane, chilled to 5° C., and filtered to yield 34 grams of the desired hydrazide as a white solid, melting point 178°–180° C.

Analysis of the hydrazide (percent by weight). Found: C, 39.6; H, 4.7; N, 10.4. Calculated: C, 39.8; H, 4.8: N, 10.3.

1-Thia-2,3-diazospiro(4.5)dec-3-ene, 4-chloro-2-(1-chloro-2,2,2-trichloroethyl)-, 1-oxide was not produced upon attempts to react the thusly prepared hydrazide with thionyl chloride in the presence of dimethylformamide, according to the general procedures of the process of the invention.

COMPARATIVE EXAMPLE B

An attempt to prepare 1-thia-2,3-diazaspiro(4.2)hepta-3-ene, 4-chloro-2-(1-chloro-2,2,2-trichloroethyl)-, 1-oxide (formula I, wherein n is one, p is zero, and each X and each Y is hydrogen) according to procedures of the process of the invention was unsuccessful, illustrating the criticality associated with the number of carbon atoms, i.e., the value of p, in the alkane ring structure of the hydrazone of the formula II.

Cyclopropanecarboxylic acid, (2,2,2-trifluoroethylidene)hydrazide was prepared by refluxing a solution containing 10.0 grams (0.10 mol) of cyclopropanecarboxylic acid hydrazide and 12.6 grams (0.11 mol) of trifluoroacetaldehyde hydrate in 350 milliliters of toluene. Water was removed as formed. After two hours, solvent was removed by rotary evaporation, and the residue was crystallized from ethanol to yield 11.5 grams of a white solid, melting point 179°–180° C.

Analysis for cyclopropanecarboxylic acid (2,2,2-trifluoroethylidene)hydrazide (percent by weight). Found: C, 40.2; H, 3.9; N, 15.8 Calculated: C, 40.0; H, 4.0; N, 15.6.

Reaction of the thusly prepared material with thionyl chloride in the presence of dimethylformamide did not result in detectable quantities of the thiadiazospiro compound.

Thiadiazoline compounds, preparation of which was made according to Examples 1–4, and unsuccessfully attempted according to Comparative Examples A and B, are summarily described in Table I.

TABLE I

| Example or Comp. Example | $R_F$ | p | n | Isomer Fraction | m.p.(°C.) | % Yield |
|---|---|---|---|---|---|---|
| 1 | $CF_3$ | 2 | 1 | (a) | 114°–117° C. | 0.8 |
| 2 | $CF_3$ | 3 | 1 | first | 99°–101° C. | 18 |
|   |        |   |   | second | 119°–121° C. | 32 |
| 3 | $C_2F_5$ | 3 | 1 | first | 92°–94° C. | 5.5 |
|   |        |   |   | second | 92°–95° C. | 35 |
| 4 | $CF_3$ | 3 | 2 | (b) | 83°–85° C. | 65 (c) |
| A | $CCl_3$ | 3 | 1 | — | — | 0 |
| B | $CF_3$ | 0 | 1 | — | — | 0 |

(a) No isomer separation was made.
(b) No diastereoisomers.
(c) Yield based on the monoxide (n = 1).

Compounds of Formula I have been found to be useful for inhibiting growth of unwanted plants, being active with respect to both broad-leaved plants and grasses. The compounds are generally most effective when applied pre-emergence, i.e., to the soil before the plants have sprouted.

For purposes of inhibiting plant growth, the compounds are applied in an effective amount to the locus. Compositions comprising a carrier or a surface-active agent, or both a carrier and a surface-active agent, in addition to at least one compound of Formula I, are preferred for use in such applications.

The term "carrier" as used herein means a solid or fluid material, which may be inorganic or organic and of synthetic or natural origin, with which the active compound is mixed or formulated to facilitate its application to the plant, seed, soil or other object to be treated, or its storage, transport or handling.

Suitable solid carriers are natural and synthetic clays and silicates, for example, natural silicas such as diatomaceous earths; magnesium silicates, for example, talcs, magnesium aluminum silicates, for example, attapulgites and vermiculites; aluminum silicates, for example, kaolinites, montmorillonites and micas; calcium carbonates; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; solid polychlorophenols; bitumen, waxes such as, for example, beeswax, paraffin wax, and chlorinated mineral waxes; and solid fertilizers, for example, superphosphates.

Examples of suitable fluid carriers are water, alcohols, such as for example, isopropanol, glycols; ketones such as, for example, acetone, methyl ethyl ketone, methyl isobutyl ketone and cyclohexanone; ethers; aromatic hydrocarbons such as, for example, benzene, toluene and xylene; petroleum fractions such as, for example, kerosene, light mineral oils; chlorinated hydrocarbons, such as, for example, carbon tetrachloride, perchloroethylene, trichloroethane, including liquefied normally vaporous gaseous compounds. Mixtures of different liquids are often suitable. The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium salts of sulfonated castor oil, and sodium alkylaryl sulfonates such as sodium dodecylbenzene sulfonate; and polymers of ethylene oxide and copolymers of ethylene oxide and propylene oxides.

The compositions may be formulated as wettable powders, dusts, granules, solutions, emulsifiable concentrates, emulsions, suspension concentrates and aerosols. Wettable powders are usually compounded to contain 25, 50 or 75% by weight of toxicant and usually contain in addition to solid carrier, 3–10% by weight of a dispersing agent, 15% of a surface-active agent and where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing ½–10% by weight of toxicant. Granules are usually prepared to have a size between 10 and 100 BS mesh (1.676–0.152 mm), and may be manufactured by agglomeration or impregnation techniques. Generally granules will contain ½–25% by weight toxicant and 0–10% by weight of additives such as stabilizers, slow release modifiers and binding agents. Emulsifiable concentrates usually contain, in addition to the solvent and, when necessary, co-solvent, 10–50% weight per volume toxicant, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75%w toxicant, 0.4–5%w of dispersing agents, 1–5% of surface-active agent, 0.1–1%w of suspending agents such as protective colloids and thixotropic agents, 0–10%w of appropriate additives such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate with water, may also be utilized in application of the compounds of the present invention. The said emulsions may be of the water-in-oil or of the oil-in-water type, and may have a thick mayonnaise-like consistency.

The compositions may also suitably contain other ingredients, for example, other compounds possessing pesticidal, especially insecticidal, acaricidal, herbicidal or fungicidal properties.

The method of applying the compounds of this invention comprises applying a compound of formula I, ordinarily in a composition of one of the aforementioned types, to a locus or area to be protected from undesirable plant growth such as the foliage of the plants or the plant growth medium, e.g., soil in which the plant is growing or is to be grown. The active compound, of course, is applied in amounts sufficient to exert the desired action.

The amount of compound of the invention to be used in controlling undesirable vegetation will naturally depend on the condition of the vegetation, the degree of activity desired, the formulation used, the mode of application, the climate, the season of the year, and other variables. Recommendations as to precise amounts are, therefore, not possible. In general, however, application to the locus to be protected of from 0.2 to 20.0 kilograms per hectare of the compound of this invention will be satisfactory.

Herbicidal activity of the spiro-$\Delta^3$-1,2,3-thiadiazoline derivatives of the invention is illustrated by Example 5.

EXAMPLE 5

Pre-emergence herbicidal activity was evaluated by planting seeds of various weed species in soil treated with a test compound according to the invention. Specifically, effects of the compounds of the invention upon seeds of barnyard grass (*Echinochloa crus-galli*), garden cress (*Lepidium sativum*), downy brome (*Bromus tectorum*), velvet leaf (*Abutilon theophrasti*), yellow foxtail (*Setaria lutescens*), and sicklepod (*Cassia obtusifolia*) were evaluated. Seeds were planted in test tubes nominally measuring 25 × 200 millimeters. In each case, the tube was filled about three-quarters full with untreated soil, which was then covered with about 2.5 cubic centimeters of soil that had been treated with one milligram of a thiadiazoline derivative test compound. Dosages of the test compound in the treated soil corresponded to application of approximately twenty pounds of the compound per acre. Seeds were planted in the treated soil which was then covered with about 1.5 cubic centimeters of untreated soil.

The planted soil was maintained under controlled conditions of temperature, moisture, and light for 9 to 10 days. Germination and growth were then observed and the influence of the test compound was rated according to the 0 to 9 scale defined as follows:

| Rating | Defined |
|---|---|
| 9 | No living tissue |
| 8 | Living tissue, but plant expected to die |
| 7 | Plant badly damaged, but expected to live |
| 6 | Plant badly damaged, but expected to recover completely |
| 5 | Unacceptable damage for crop plants, insufficient damage to weeds |
| 3–4 | Definite damage |
| 1–2 | Plant slightly affected, possibly by the chemical, possibly due to biological variability |
| 0 | No visible effect. |

Plant damage, for purposes of the rating scale, was evaluated in comparison to germination and growth of control plantings of the various species in test tubes containing only untreated soil.

Pre-emergence herbicidal activity of certain thiadiazoline derivatives of the invention is indicated by the following tabulated ratings for plant species and compounds tested under these procedures:

| Test Compounds, According to Formula I | | | | | | | Weed Species | | | | | |
|---|---|---|---|---|---|---|---|---|---|---|---|---|
| $R_F$ | p | n | X | Y | Z | isomer M.p.* | Barnyard Grass | Garden Cress | Downy Brome | Velvet Leaf | Yellow Foxtail | Sicklepod |
| $CF_3$ | 3 | 1 | H | H | Cl | 100°–102° C. | 7 | 5 | 9 | 9 | 7 | — |
| $CF_3$ | 3 | 1 | H | H | Cl | 119°–121° C. | 8 | 9 | 8 | 9 | 8 | 8 |
| $CF_3$ | 3 | 2 | H | H | Cl | 83°–85° C. | 4 | 4 | 8 | 5 | 3 | 2 |
| $C_2F_5$ | 3 | 1 | H | H | Cl | 92°–94° C. | 8 | 3 | 8 | 6 | 0 | 0 |

| Test Compounds, According to Formula I | | | | | | | Weed Species | | | | | |
|---|---|---|---|---|---|---|---|---|---|---|---|---|
| $R_F$ | p | n | X | Y | Z | isomer M.p.* | Barnyard Grass | Garden Cress | Downy Brome | Velvet Leaf | Yellow Foxtail | Sickle-pod |
| $C_2F_5$ | 3 | 1 | H | H | Cl | 92°–95° C. | 8 | 6 | 8 | 7 | 0 | 4 |

*Isomer fractions are identified by their melting points as noted in Examples 1–4.

ILLUSTRATIVE EMBODIMENT 1

In further illustration of the invention, upon the reaction of a compound of formula

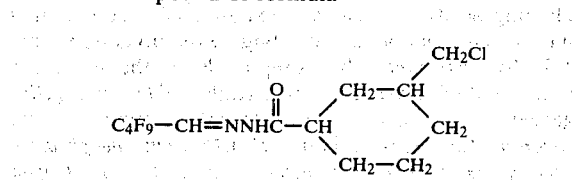

with thionyl chloride according to the general procedures of Examples 1–3, there is obtained the herbicidally active thiadiazoline derivative of the formula

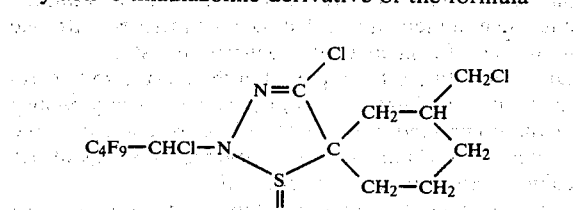

ILLUSTRATIVE EMBODIMENT 2

If reaction between thionyl chloride and a hydrazone of the formula

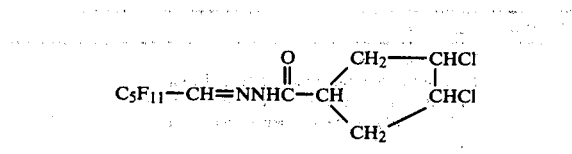

is conducted according to procedures of Example 1–3, there is obtained a thiadiazoline, of the formula

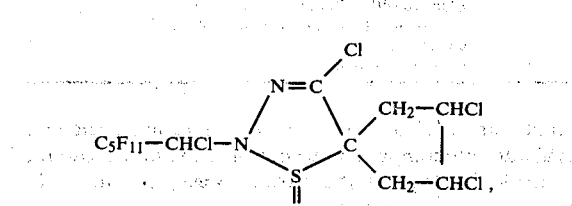

having activity as a herbicide.

ILLUSTRATIVE EMBODIMENT 3

Upon mixing of thionyl chloride and the hydrazone

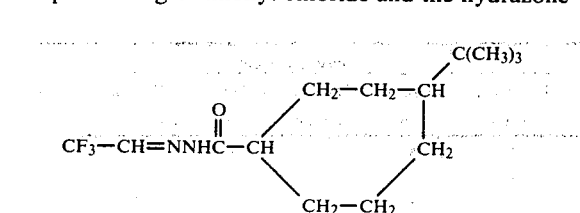

under general procedures of Examples 1–3 there is prepared the herbicidally active thiadiazoline derivative

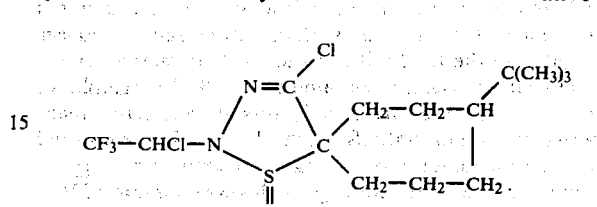

ILLUSTRATIVE EMBODIMENT 4

If reaction of thionyl bromide and a hydrazone of the formula

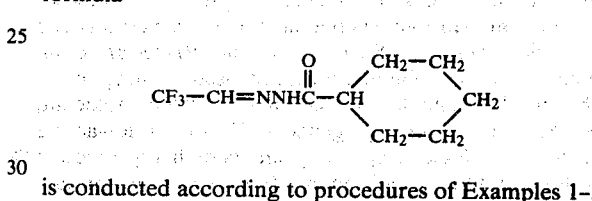

is conducted according to procedures of Examples 1–3, there is obtained a thiadiazoline of the formula

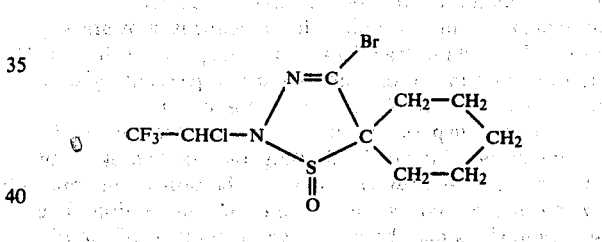

having activity as a herbicide.

We claim as our invention:

1. A compound of the formula $$R_F-CHCl-N\underset{\underset{(O)_n}{\downarrow}}{\overset{N=C}{\underset{S}{\bigg|}}}\overset{Z}{\underset{CXY}{C}}(CXY)_p$$

wherein
  $R_F$ represents a perfluoroalkyl group having from 1 to 6 carbon atoms, inclusive,
  each X and each Y is independently selected from the group consisting of hydrogen, halogens, lower alkyl having from 1 to 4 carbon atoms inclusive, and halogensubstituted lower alkyl having from 1 to 4 carbon atoms, inclusive,
  Z is selected from the class consisting of fluorine, chlorine, and bromine,
  p is an integer from 2 to 6, inclusive, and
  n is the integer one or the integer two.

2. A compound of the formula

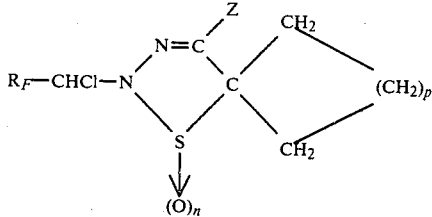

wherein
- $R_F$ represents a perfluoroalkyl group having from one to four carbon atoms, inclusive,
- Z is selected from the class consisting of fluorine, chlorine, and bromine,
- p is an integer from two to four, inclusive, and
- n is the integer one or the integer two.

3. The compound of claim 2, wherein
- $R_F$ represents a perfluoroalkyl group having from one to three carbon atoms, inclusive, and
- p is the integer two or the integer three.

4. The compound of claim 3, wherein
- $R_F$ represents a perfluoroalkyl group having one or two carbon atoms.

5. The compound of claim 1, 2, 3, or 4, wherein Z is chlorine.

6. A process for the preparation of spiro-$\Delta^3$-1,2,3-thiadiazoline derivatives, which comprises reacting a compound selected from the class consisting of thionyl fluoride, thionyl chloride and thionyl bromide with an acylated perfluoroaliphatic aldehyde hydrazone of the formula

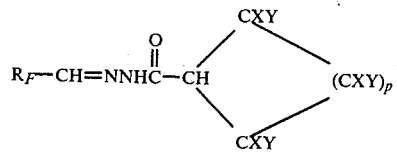

wherein
- $R_F$ is a perfluoroalkyl group having from 1 to 6 carbon atoms, inclusive,
- each X and each Y is independently selected from the group consisting of hydrogen, halogens, lower alkyl having from 1 to 4 carbon atoms, inclusive, and halogen-substituted lower alkyl having from 1 to 4 carbon atoms, inclusive, and
- p is an integer from 2 to 6, inclusive.

* * * * *